United States Patent
Martorell Pena et al.

(10) Patent No.: US 8,802,385 B2
(45) Date of Patent: Aug. 12, 2014

(54) SUSPENSION MEDIUM FOR RED BLOOD CELLS COMPRISING AMINO ACIDS

(75) Inventors: Daniel Martorell Pena, Barcelona (ES); Ma del Carmen Traves Polo, Barcelona (ES); Jordi Farre Leon, Barcelona (ES); Josefina Castells Parera, Barcelona (ES)

(73) Assignee: Grifols, S.A., Barcelona (ES)

( * ) Notice: Subject to any disclaimer, the term of this patent is extended or adjusted under 35 U.S.C. 154(b) by 1875 days.

(21) Appl. No.: 11/766,934

(22) Filed: Jun. 22, 2007

(65) Prior Publication Data
US 2007/0298406 A1 Dec. 27, 2007

(30) Foreign Application Priority Data
Jun. 22, 2006 (ES) .................................. 200601682

(51) Int. Cl.
*A01N 1/02* (2006.01)
*G01N 33/80* (2006.01)
*G01N 33/96* (2006.01)

(52) U.S. Cl.
CPC ................ *G01N 33/80* (2013.01); *G01N 33/96* (2013.01)
USPC ........................................... 435/7.25; 436/18

(58) Field of Classification Search
CPC ............................... G01N 33/80; G01N 33/96
See application file for complete search history.

(56) References Cited

U.S. PATENT DOCUMENTS

| 4,379,847 A * | 4/1983 | Fruitstone et al. | ................ 436/8 |
| 2006/0292544 A1 * | 12/2006 | Hassanein et al. | ................ 435/2 |

FOREIGN PATENT DOCUMENTS

| EP | 194212 | 9/1986 |
| EP | 0266194 | 5/1988 |
| EP | 305337 | 3/1989 |
| EP | 485228 | 5/1992 |
| EP | 755719 | 1/1997 |
| ES | 2126521 | 3/1999 |
| WO | 2004/072306 | 8/2004 |

OTHER PUBLICATIONS

Greenwalt et al., "The effect of hypotonicity, glutamine, and glycine on red cell preservation" Transfusion 37:269-276 (1997).*
Allan et al., "The preservation of red cell antigens at low ionic strength", Transfusion 30(5):423-426 (1990).*
Neppert et al. "Unsatisfactory Detection of an in vivo Haemolytic Anti-Vel by the Gel Test", Vox Sanguinis 75 : 70-71 (1998).*
Grey, et al. "Comparison of Low Ionic Diluents for Use With the Diamed Antiglobulin Gel Test." Transfusion Medicine, 2002, vol. 12, No. 1, pp. 63-69.
De Castilho, et al. "Evaluation of Recent Techniques for Detection of Red Blood Cell Antibodies in Sera of Reference Samples, Patients, Pregnant Women, and Blood Donors." J. Clin. Lab. Anal., 1996, vol. 10, No. 5, pp. 250-256.
Federation Espanola de donantes de sangre (Spanish Blood Donor Federation) www.donantesdesangre.net, Jul. 2005.
Global Database on Blood Safety: Report 2001-2002. Blood Transfusion Safety, Essential Health Technologies, World Health Organization. Geneva, Switzerland.
Y, Lapierre et al., The gel test: A new way to detect cell antigen-antibody reactions, Transfusion 33:639-643 (1990).

* cited by examiner

*Primary Examiner* — Sandra Saucier
(74) *Attorney, Agent, or Firm* — Leason Ellis LLP

(57) ABSTRACT

The present invention relates to a new suspension medium or diluent solution for red blood cells for use in haematological methods. The suspension medium or diluent solution for red blood cells may comprise a combination of two or more amino acids of any group, and preserves the red blood cells in the sample for at least 8 weeks.

13 Claims, No Drawings

SUSPENSION MEDIUM FOR RED BLOOD CELLS COMPRISING AMINO ACIDS

CROSS-REFERENCE TO RELATED APPLICATIONS

This application claims priority to Spanish patent application Ser. No. 200601682 filed Jun. 22, 2006, the contents of which are hereby incorporated by reference in their entirety.

DESCRIPTION

1. Field of the Invention

The present invention concerns a new suspension medium for red blood cells, for carrying out the main immunohaematological agglutination tests requiring erythrocytes which are performed in hospitals and blood-transfusion centres. The determination of the serum group, the detection and identification of irregular antibodies, the preparation of positive and negative controls, and the need to preserve samples for investigation of anomalous results, require red blood cells, re-suspended in an aqueous medium, which maintain their functionality.

2. State of the Art

The clinical advance provided by blood transfusion brought with it a development of immunohaematology. Without this, the number of transfusions which are carried out at present on accident victims, in surgery or in the treatment of leukaemia, cancer and other illnesses would not have been possible. In Spain, during 2004 a total of 1.6 million blood donations were made (1), in the U.S., it is estimated that around 15 million bags of blood are donated per year (2) and the World Health Organisation, on the basis of data from 178 countries, estimates at 81 million the total blood units donated annually (3). This number of donations would be of no use without prior immunohaematological determination. The main blood groups which are determined are the ABO system and the RH system, and particularly of this second system, antigen D (RH1).

In an emergency situation, all individuals may receive red blood cells or red corpuscles of group O, and AB individuals may receive red blood corpuscles of any ABO group. Hence, individuals of group O are known as universal donors and AB individuals as universal recipients. The acceptance of red corpuscles or red blood cells coming from a person of a particular blood group by another person is conditional on the antibodies present in the plasma of the recipient. Thus, individuals of group O have antibodies against antigens A and B, individuals of group A have antibodies against B, and vice versa for individuals of group B, and individuals of group AB do not have antibodies. Consequently, it is not the red blood cells, but the plasma of AB individuals that can be donated to all blood groups.

The basis of immunological analysis is then the determination of the ABO group and the RH group. The ABO system is determined by antigens and antibodies (known as regular antibodies), while the RH system and the other systems only have antibodies (known as irregular antibodies) as a consequence of pregnancy and of transfusion practice. However, in spite of their low frequency in the population, the determination of irregular antibodies is of the utmost importance, and is being implemented in all hospitals and blood transfusion centres in order to avoid risks and to obtain extremely safe transfusions. Neonatal determinations have also been implemented, both for diagnosing possible haemolytic diseases of the newborn, and also for prophylaxis to be given to the mother in the event that she is Rh− (lack of antigen D) and the child is Rh+ (exhibits antigen D).

In immunohaematology, the introduction of new technologies for typing red blood cells, compatibility tests and detection of regular and irregular antibodies have represented the most significant advances in this area. The improvements have been related to the components which favour specific agglutination (e.g. Coombs solution, LISS solution (low ionic strength solution), solutions with albumin, solutions with proteolytic enzymes or other potentiators of the antigen-antibody union), the improvement of reactive antibodies (e.g. monoclonal antibodies), and also new or substantially different methodologies becoming available for displaying agglutination (e.g. micro-sheet and gel technique). The appearance of the technique of microtubes in a column, also known as gel or card technique, provides the basis for the modernisation of immunohaematology. Since its appearance in 1986, the technique of microtubes in a column (4) has not ceased to experience spectacular growth. Owing to its ease of automation, this methodology will displace the rest of the techniques, being forecast as the only one which will remain for phenotypic determination. Together with the genotypic technique which prevails, they will form the basis for immunological analysis. At present, the majority of methodologies for genotypic determination are in the preliminary stages, at all events limited to research laboratories.

The gel technique separates the agglutinated cells from those which have not agglutinated, via centrifuging in a filtration matrix formed by small balls of gel (EP 194212, EP 305337), of glass or other spherical material (EP 485228, EP 725276, EP 755719). In the upper part of the microtube, the reaction chamber, located above the gel column, the samples are dispensed. In the column in which the gel or filtration matrix is contained, there is a buffered solution which, depending on the analysis, may contain specific antibodies (e.g. anti-A, anti-B or anti-D) or human antiglobulin (human anti-IgG or anti-IgM antibodies), known as Coombs solution. The filtration matrix is composed of spherical particles which settle in a buffered aqueous solution. In order to display the immunohaematological agglutination, centrifuging is carried out, forcing the cells (red blood cells) to pass through the filtration matrix. The space which remains between particles is large enough to allow the cells which have not agglutinated, that is, individual cells, to pass through. While in the event that agglutination has taken place, the agglutinated cells are retained between the balls. Although, strictly, it is a qualitative technique, the passage through the filtration matrix makes it possible to distinguish different degrees of agglutination. In positive samples in the upper part of the gel the very strong agglutinates will be retained, while the weak agglutinates may pass a certain distance through the matrix, remaining half-way, for example. The absence of agglutination will mean that all the cells reach the base of the microtube (negative reaction). As occurs in conventional immunohaematology, owing to the intense red colour of the red blood cells, the technique does not require any marker or amplifier of the antigen (red blood cells)—antibody union.

The gel technique has made it possible to physically separate the positive results from the negative results, i.e. the positives in the upper part of the gel (high intensity agglutinate), along the column (medium or weak agglutinates), and in the lower part of the column the negative results (non-agglutinated red blood cells).

In the immunohaematological tests for detecting regular and irregular antibodies in plasma or serum, reagent red blood cells are used. Said red blood cells are prepared in a solution for the purpose of maintaining their functionality and integrity for a certain period of time, customarily between 1 and 4 weeks. In the blood bank laboratories or those responsible for blood transfusion, the red blood cells with specific antigens are selected so that they can act as reagent red blood cells in each of the immunohaematological tests. The combinations necessary for preparing the screening cells, assembly of 2, 3 or 4 red blood cells with concrete antigenic specificities which make it possible to detect antibodies, or panels, assembly of 11 or more red blood cells which make it possible to identify the specificity of the antibodies detected, are not easy to produce and they may also prove of difficult execution in medium-sized centres. The difficulties of obtaining said screening cells or panels, added to the need to prepare these reagent red blood cells frequently, are very familiar to any expert in the field, as is the essential need to have available a suspension solution for red blood cells or a diluent for red blood cells. In addition, screening cells or panels are also prepared with an enzymatic treatment (e.g. papainization) in order to potentiate the reactivity of specific blood groups. The blood groups potentiated by this treatment are well known to any expert in the field.

Diluent solutions are currently used which are variations on the original Alsever solution. These solutions generally contain an anticoagulant (e.g. citrate), a phosphate buffer, an energy source (e.g. glucose), purines and nucleosides (e.g. adenine and inosine), sodium chloride, and preservatives (antibiotics). However, the reagent red blood cells prepared with these conventional solutions may present problems in gel technology. The physical separation which has permitted gel technology may be affected, since some of the non-agglutinated red blood cells are often retained along the column. This non-specific retention produces false positive results, since it is confused with a medium or weak agglutinate.

The suspension solution for the reagent blood cells should make it possible to maintain the functional characteristics and their capacity for passing through the gel column to the lower part of the column in the event that they have not agglutinated. These characteristics should be maintained for the maximum time possible, owing to the previously stated difficulties of preparing red blood cells in immunohaematology laboratories. The parameters which must be maintained constant over this period are, among others, the pH, the osmolarity and the ionic strength. Likewise, it is essential to provide glucose and adenine so that the red blood cells maintain their viability. The assembly and concentration of these substances bring about an increase in the ionic strength which is reduced by the addition of glycine. The red blood cells have lost the genetic nucleus and any capacity for biosynthesis, so that the addition of this amino acid is in no way related to protein synthesis.

DESCRIPTION OF THE INVENTION

In the research carried out by the inventors in order to reduce the loss of specificity which is observed in reagent red blood cells, it was surprisingly discovered that the addition to these diluent solutions for reagent red blood cells of combinations of amino acids apart from glycine, in concentrations higher than those necessary for reducing the ionic strength, makes it possible to reduce the loss of specificity which is observed in reagent red blood cells, that is, considerably reduces the non-specific retention of non-agglutinated red blood cells along the gel column.

For this reason, a description will be given in the present patent application of the compositions of diluent solutions for reagent red blood cells which make it possible to maintain the integrity and functionality of the reagent red blood cells over a prolonged period of time, for example, 8 weeks. During this period of time, the red blood cells preserve their capacity for passing through the gel or any other narrow space and the capacity for not agglutinating non-specifically, maintaining the characteristic of deformability, integrity and antigenicity, so that they can be used as an immunohaematological reagent for the determination of the serum group, a test for detecting regular antibodies, and in the investigation and identification of irregular antibodies.

The incorporation of the combinations of amino acids according to the invention in a diluent solution or suspension medium for red blood cells maintains the red blood cells in a state of integrity and with characteristics of functionality which permit their use in gel technology. The passage of the red blood cells through a gel matrix exhibits no difference in retention between the fresh red blood cells (initial preparation time for the suspension) and those kept for 8 weeks. That is, the amino acids incorporated in the diluent solution make it possible to maintain in the red blood cells the initial physical characteristics of the fresh red blood cells. The longer the preparation of red blood cells takes, the more possibilities exist for the appearance of false positive results. The reagent red blood cells are living cells, so that degradation in a relatively short time is very well known to any expert in the field.

The gel technique permits visual quantification between agglutinates of different size. The results of agglutination are customarily designated by a score graduation similar to that of Table 1. As described previously, non-agglutinated red blood cells, red blood cells which should be found at the bottom of the column, may present results similar to +/− and 1+ which would give an incorrect diagnosis, an incorrect positive interpretation.

TABLE 1

| Interpretation | Grade | Score | Description |
| --- | --- | --- | --- |
| Negative: | − | 0 | Band of red blood cells at the bottom of the column, rest of column without visible agglutinates. |
| Positive: | +/− | 3 | Sparse agglutinates of small size in the lower half of the column, with red blood cells at the bottom of the column. |
|  | 1+ | 5 | Some agglutinates of small size in the column. |
|  | 2+ | 8 | Agglutinates of small or medium size along the column. |
|  | 3+ | 10 | Upper band of agglutinates, of medium size, in the upper half of the column. |
|  | 4+ | 12 | Band of agglutinated red blood cells in the upper part of the column. |

The addition of the combinations of amino acids according to the present invention to a liquid which contains the customary constituents known to any expert in the field, considerably reduces non-specific retentions of the reagent red blood cells. These constituents are phosphate buffer, sodium chloride, glucose, adenine, preservatives (e.g. chloramphenicol and neomycin), EDTA and glycine.

The concentration of each of the amino acids which form the amino acid combinations of the present invention may vary according to their solubility in aqueous solutions and such that, as a whole, the total osmolarity of the diluent solution for red blood cells is within a range of 100-700 milliosmol/kg.

A description will now be given of examples of combinations of amino acids in a suspension solution for red blood cells according to the present invention. For example, if in a base liquid without amino acids other than glycine (liquid No. 1) amino acids are added (liquid No. 2), the total number of false positives obtained in 50 individual determinations over 10 weeks is reduced from 13 to zero in a screening of two cells by the Coombs technique for irregular antibodies. It should be mentioned that 10 weeks from the manufacture of the reagent red blood cells is a period which exceeds the conventional limits for preservation of the reagent red blood cells. Another way of quantifying the differences between liquids is to compare the average scores obtained from all the individual determinations. The average scores obtained in 50 determinations of 10 phials evaluated over 10 weeks for liquid No. 1 and liquid No. 2 are, respectively, 2.44 and 1.52. For a screening technique of 2 cells with papainized red blood cells, the number of false positives is reduced from 40 to 7 between the liquid without amino acids (liquid No. 1) and the liquid with amino acids (liquid No. 2). The 7 false positives were obtained in week 10, while the false positives for liquid No. 1 are obtained in shorter times from the preparation of the suspension. Comparing the average scores in this screening technique of 2 cells with papainized red blood cells also clearly shows the differences between liquids, the average score value of 50 determinations for liquid No. 1 and liquid No. 2 being 5.92 and 1.84 respectively.

| Liquid No. 1 | |
| --- | --- |
| Ingredients | Concentration (g/l) |
| $KH_2PO_4$ (anhydrous monopotassium phosphate) | 1.36 |
| $Na_2HPO_4$ (disodium phosphate) | 1.42 |
| Chloramphenicol | 0.17 |
| Neomycin | 0.10 |
| NaCl | 1.0 |
| Dextrose (anhydrous D-glucose) | 3.5 |
| Adenine | 0.02 |
| EDTA (dihydrated disodium) | 2.80 |
| Glycine | 14.70 |

| Liquid No. 2 | |
| --- | --- |
| Ingredients | Concentration (g/l) |
| $KH_2PO_4$ (anhydrous monopotassium phosphate) | 1.36 |
| $Na_2HPO_4$ (disodium phosphate) | 1.42 |
| Chloramphenicol | 0.17 |
| Neomycin | 0.10 |
| NaCl | 1.0 |
| Dextrose (anhydrous D-glucose) | 3.5 |
| Adenine | 0.02 |
| EDTA (dihydrated disodium) | 2.80 |
| Glycine | 14.70 |
| L-valine | 3.20 |
| L-methionine | 2.52 |
| L-leucine | 2.60 |
| L-isoleucine | 6.48 |

If in a base liquid (e.g. liquid No. 1), apart from the amino acids, other components described and widely used in red blood cell solutions are incorporated, such as inosine, citrate, citric acid and bicarbonate (e.g. liquid No. 3), the effect of the amino acids may be even greater. In the case of a screening of two cells by the Coombs technique for irregular antibodies, no false positives are obtained in 50 determinations over 10 weeks, and the average score is 0.96. Nor in the screening of two papainized cells are false positives obtained, and the average score is 0.80.

| Liquid No. 3 | |
| --- | --- |
| Ingredients | Concentration (g/l) |
| $KH_2PO_4$ (anhydrous monopotassium phosphate) | 0.30 |
| $Na_2HPO_4$ (disodium phosphate) | 0.28 |
| Chloramphenicol | 0.17 |
| Neomycin | 0.10 |
| NaCl | 1.00 |
| Dextrose (anhydrous D-glucose) | 3.50 |
| Adenine | 0.02 |
| EDTA (dihydrated disodium) | 2.80 |
| Inosine | 0.02 |
| $NaHCO_3$ | 0.80 |
| $Na_3$ dihydrated citrate | 2.00 |
| Monohydrated citric acid | 0.18 |
| Glycine | 6.00 |
| L-valine | 3.20 |
| L-methionine | 2.52 |
| L-leucine | 2.60 |
| L-isoleucine | 6.48 |

It has been stated (5) that specific antigens of blood groups (M, Pl, $Fy^a$, $Fy^b$, S and s) may be lost or reduce their antigenicity on re-suspending the red blood cells in solutions of low ionic strength. The addition of amino acids does not alter the expression of said antigens, the same reactivity, antigenic potency, being observed from the preparation of the suspension up to 10 weeks later, i.e. during the useful life of the product.

The haemolysis observed in the liquids which incorporate amino acids is lower than that obtained with the liquid without amino acids or only with glycine. This indicates that the addition of these substances does not have a negative effect on the osmotic fragility of the cell.

In the case of the reagent red blood cells for the determination of the serum group, that is, the detection of regular antibodies, the suspensions of red blood cells which incorporate amino acids exhibit correct functioning.

In serum group techniques with a base liquid without amino acids other than glycine, liquid No. 1, in 240 determinations using 4 serum group cells ($A_1$, $A_2$, B and O) over 10 weeks, 187 false positives were obtained, while if amino acids are added, liquid No. 2 and liquid No. 3, the total number of false positives is reduced to zero. The false positives of liquid No. 1 are obtained starting from 2 and 4 weeks from the preparation of the suspension of red blood cells, while with the liquids which incorporate amino acids, 10 weeks from their manufacture, still no false positives are observed. The average scores from 240 determinations using 4 serum group cells, with 10 phials for each cell, evaluated over 10 weeks for liquid No. 1, liquid No. 2 and liquid No. 3 are, respectively, 4.06, 1.37 and 0.94.

The addition of amino acids other than valine, leucine, isoleucine and methionine, including non-polar aliphatics and those which contain sulphur, also has the effect of reducing non-specific retentions. For example, with liquid No. 4, which contains non-polar aliphatic amino acids, aromatic amino acids, hydrophilic amino acids and polar amino acids with positive, negative or neutral charge, a reduction in non-specific retentions of red blood cells in the gel column is likewise obtained.

| Liquid No. 4 | |
| --- | --- |
| Ingredients | Concentration (g/l) |
| $KH_2PO_4$ (anhydrous monopotassium phosphate) | 0.30 |
| $Na_2HPO_4$ (disodium phosphate) | 0.28 |
| Chloramphenicol | 0.17 |

-continued

Liquid No. 4

| Ingredients | Concentration (g/l) |
|---|---|
| Neomycin | 0.10 |
| NaCl | 1.00 |
| Dextrose (anhydrous D-glucose) | 3.50 |
| Adenine | 0.02 |
| EDTA (dihydrated disodium) | 2.80 |
| Inosine | 0.02 |
| NaHCO$_3$ | 0.80 |
| Na$_3$ dihydrated citrate | 2.00 |
| Monohydrated citric acid | 0.18 |
| Glycine | 6.00 |
| L-valine | 1.60 |
| L-methionine | 1.26 |
| L-leucine | 1.30 |
| L-isoleucine | 3.24 |
| L-phenylalanine | 2.00 |
| L-lysine | 1.22 |
| L-histidine | 0.50 |
| L-tryptophan | 0.50 |
| L-arginine | 1.60 |
| L-threonine | 1.10 |

By means of the present invention it has been possible to increase significantly the useful life in storage of suspensions of red blood cells for the purpose of analysis, from the customary period of four weeks to a minimum period of eight weeks, as shown by the tests performed.

BIBLIOGRAPHY (1) Federación Espanola de donantes de sangre (Spanish Blood Donor Federation). www.donantesdesangre.net. July 2005.
(2) *Facts about blood*. American Association of Blood Banks (2004).
(3) *Global Database on Blood Safety: Report* 2001-2002. Blood Transfusion Safety, Essential Health Technologies, World Health Organization. Geneva, Switzerland.
(4) *The gel test: A new way to detect cell antigen-antibody reactions*. Y. Lapierre et al. Transfusion 33:639-643 (1990).
(5) *The preservation of red cell antigens at low ionic strength*. J. C. Allan et al. Transfusion 30:423-426 (1990).

Although the invention has been described with respect to preferred exemplary embodiments, these should not be regarded as limiting the invention, which will be defined by the widest interpretation of the following claims.

The invention claimed is:

1. A suspension medium or diluent solution for reagent red blood cells, comprising phosphate buffer, sodium chloride, glucose, adenine, at least one preservative, EDTA and glycine and a combination of two or more amino acids of any group, wherein the amino acids other than glycine are present in a concentration of 0.50 to 6.48 g/l resulting in a total osmolality of between about 100-700 milliosmol/kg for the suspension medium or diluent solution and the combination of two or more amino acids other than glycine in the suspension medium or diluent solution reduces the loss of specificity and non-specific retention of the reagent red blood cells, and maintains the integrity and functionality of the reagent blood cells.

2. The suspension medium or diluent solution for reagent red blood cells according to claims 1 further comprising inosine, citrate, citric acid and bicarbonate.

3. The suspension medium or diluent solution for reagent red blood cells according to claim 1, wherein the combination of two or more amino acids comprises a combination of aliphatic amino acids.

4. The suspension medium or diluent solution for reagent red blood cells according to claim 3, wherein the combination of aliphatic amino acids is selected from the group consisting of: L-alanine, L-valine, L-leucine and L-isoleucine.

5. The suspension medium or diluent solution for reagent red blood cells according to claim 1, wherein the combination of two or more amino acids is selected from the group consisting of aliphatic amino acids, aromatic amino acids and amino acids which contain sulphur.

6. The suspension medium or diluent solution for reagent red blood cells according to claim 5, wherein the combination comprises a combination of aliphatic amino acids and amino acids selected from the group consisting of: L-phenylalanine, L-tyrosine, L-tryptophan, L-methionine and L-cysteine.

7. The suspension medium or diluent solution for reagent red blood cells according to claim 1, wherein the combination of two or more amino acids comprises: L-valine, L-methionine, L-leucine, and L-isoleucine.

8. The suspension medium or diluent solution for reagent red blood cells according to claim 1, wherein the combination of two or more amino acids comprises a combination of hydrophobic and hydrophilic amino acids.

9. The suspension medium or diluent solution for reagent red blood cells according to claim 1, wherein the combination of two or more amino acids comprises a combination of aliphatic amino acids and amino acids selected from the group consisting of chargeless, positively charged and negatively charged polar amino acids.

10. The suspension medium or diluent solution for reagent red blood cells according to claim 9, wherein the combination of two or more amino acids comprises a combination of aliphatic amino acids and of the amino acids: L-serine, L-threonine, L-cysteine, L-methionine, L-asparagine, L-glutamine, L-lysine, L-arginine, L-histidine, L-aspartic acid and L-glutamic acid.

11. The suspension medium or diluent solution for reagent red blood cells according to claim 1, wherein the combination of two or more amino acids comprises a combination of aliphatic amino acids, and of polar, neutral or charged amino acids (positive and/or negative), and aromatic amino acids.

12. The suspension medium or diluent solution for reagent red blood cells according to claim 1, wherein the combination of two or more amino acids comprises a combination of non-polar and polar amino acids.

13. A method for preserving red blood cells comprising mixing a red blood cell sample in the suspension medium or diluent solution of claim 1, thereby preserving the red blood cells in the sample as a hematological reagent for at least 8 weeks.

* * * * *